Figure 1:
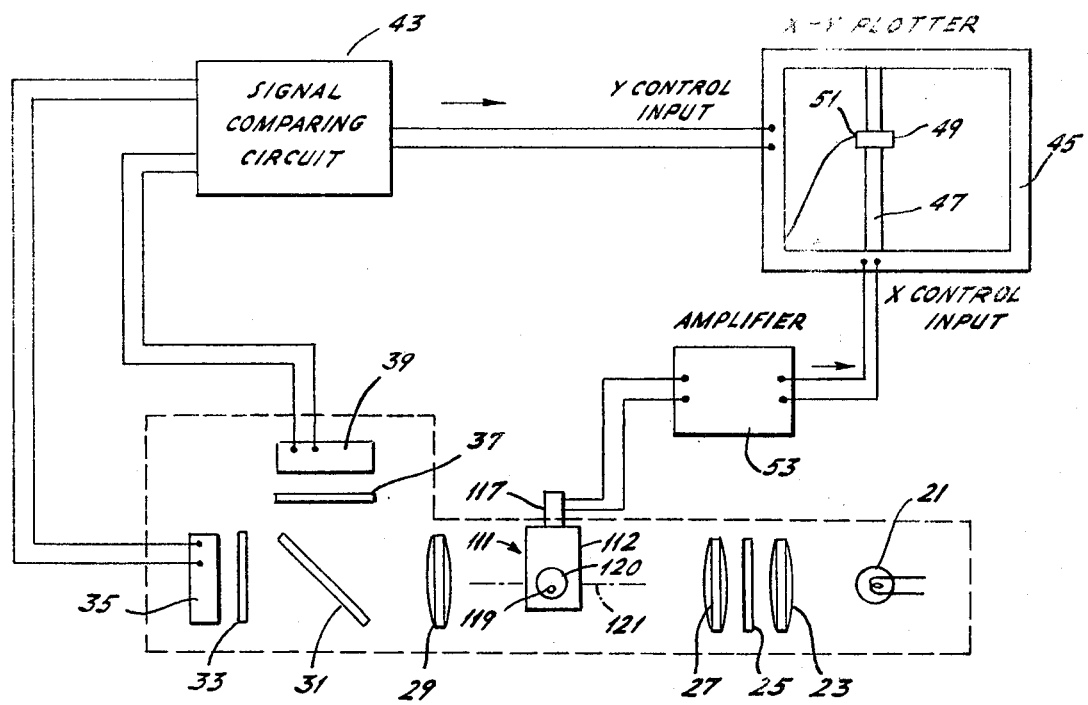

United States Patent [19]

Blume et al.

[11] 4,411,523

[45] Oct. 25, 1983

[54] CUVETTE FOR BLOOD OXYGEN ANALYSIS APPARATUS

[75] Inventors: Horst K. Blume, Huntingdon Valley; Toshio Asakura, Bala Cynwyd, both of Pa.

[73] Assignee: Technical Consulting Services, Southampton, Pa.

[21] Appl. No.: 328,057

[22] Filed: Dec. 7, 1981

Related U.S. Application Data

[63] Continuation-in-part of Ser. No. 28,790, Apr. 11, 1979, Pat. No. 4,304,488, which is a continuation-in-part of Ser. No. 845,686, Oct. 26, 1977, abandoned.

[51] Int. Cl.³ ................. G01N 33/48; G01N 21/03
[52] U.S. Cl. ............................ 356/246; 356/41
[58] Field of Search ............... 356/39, 40, 41, 246, 356/427

[56] References Cited

U.S. PATENT DOCUMENTS

| 3,779,708 | 12/1973 | Runck et al. | 356/41 X |
|---|---|---|---|
| 3,787,121 | 1/1974 | Lowy et al. | 356/41 X |
| 3,854,878 | 12/1974 | Riesow | 356/41 X |
| 4,013,417 | 3/1977 | Raffaele | 356/41 |
| 4,066,361 | 1/1978 | Achter | 356/41 |

Primary Examiner—Vincent P. McGraw
Attorney, Agent, or Firm—John J. Simkanich

[57] ABSTRACT

An improved cuvette unit suitable for use in blood oxygen analyzing and plotting apparatus in accordance with U.S. Pat. No. 4,304,488. A cuvette cavity, preferably cylindrical, is formed in a transparent plastic block. A Clark electrode is embedded in said block and arranged to project into the interior of the cavity. A horizontally-directed gas inlet is introduced adjacent the bottom of the cavity, for introducing the gas (oxygen, or an inert gas) and also providing efficient agitation. Among the benefits are the avoidance of mechanical agitation elements and the speeding up of the oxygen association and dissociation tests.

4 Claims, 2 Drawing Figures

CUVETTE FOR BLOOD OXYGEN ANALYSIS APPARATUS

This application is a continuation-in-part of application Ser. No. 28,790, filed Apr. 11, 1979, issuing as U.S. Pat. No. 4,304,488 on Dec. 8, 1981, said application Ser. No. 28,790 being a continuation-in-part of application Ser. No. 845,686 filed Oct. 26, 1977, now abandoned.

The present invention relates to the attainment of great efficiency in the measurement of the oxygen exchange property of normal and abnormal red cell hemoglobin in whole blood or hemolysate. More particularly, it relates to the measuring and plotting, at relatively high speeds, of the change in blood oxygen partial pressure to which the blood sample is subjected.

As described in U.S. Pat. No. 4,304,488 (of which this application is a continuation-in-part), a minute blood sample to be tested is put into a specially prepared serum substitute so that the blood is placed under physiologic conditions. The vessel in which this solution is contained is provided with fluid agitation, oxygen partial pressure measuring means, and an arrangement for changing oxygen content within the vessel. Light transmitted through the liquid contained in this vessel is subjected to photometric analysis involving a comparison of the light intensities at two selected wave lengths. By plotting the resultant photometric measurement against the oxygen partial pressure, one is provided with a curve showing the performance of the blood sample with respect to its oxygen association or dissociation characteristics. The process may be run each way, demonstrating minimum hysteresis and maximum reproducibility of blood oxygen dissociation and association tests. Preferably, means for maintaining the temperature of the blood sample serum is also provided.

The present invention relates to an improvement in the transparent vessel provided for containing the blood sample in the specially prepared serum substitute solution. It is usable in the apparatus described in application Ser. No. 28,790 which is issuing as U.S. Pat. No. 4,304,488, and when used therein, provides the advantages of elimination of mechanical agitating elements and the speeding up of the oxygen-exchange procedure.

A principal object of the present invention is to provide more efficient cuvette apparatus for inclusion in a blood oxygen analyzer of the type shown and described in U.S. Pat. No. 4,304,488, thereby rendering the analyzer system more efficient and effective.

Another object is to provide a blood oxygen analyzer with such an improved cuvette as to achieve greater speed of analysis.

Yet another object is to provide, in a blood oxygen analyzer, a cuvette free from any mechanical parts, and affording maximum safety to the blood sample under test, while providing efficient agitation of the solution under test.

Figure 2:
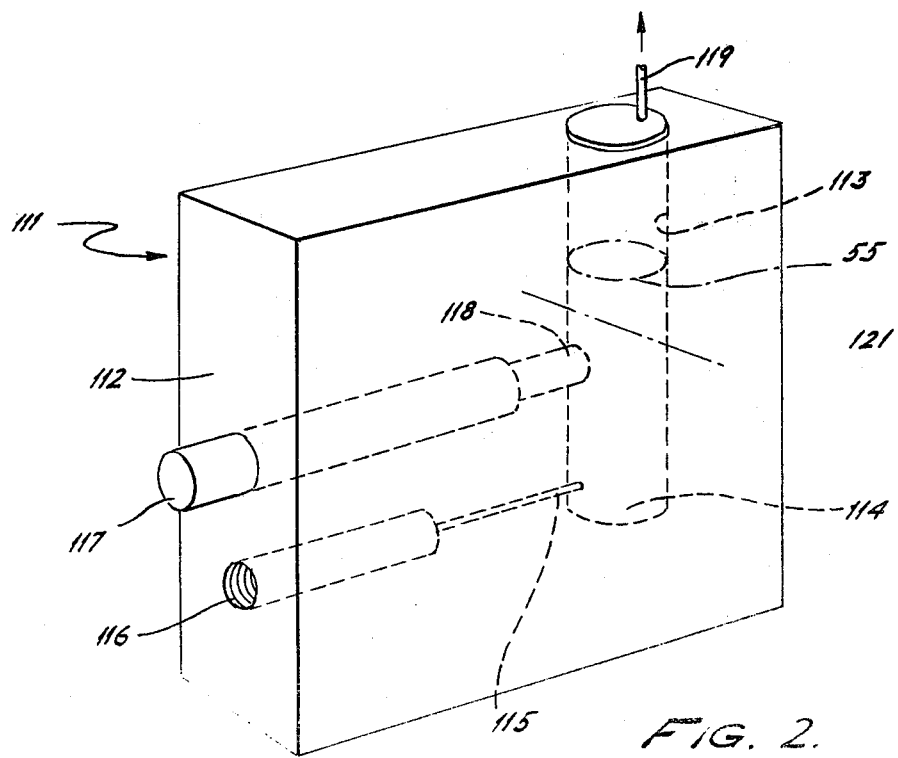

In the accompanying drawing,

FIG. 1 is a general diagram of the blood oxygen apparatus including the improved cuvette of the present invention; and FIG. 2 is an enlarged isometric view (partially in phantom lines) of the improved cuvette apparatus of the present invention.

Referring now to FIGS. 1 and 2, vessel 111 is provided for containing the blood sample in the specially prepared serum substitute solution. To this vessel 111 are connected a gas vent tube 119 and a gas introduction connection (not shown). A Clark electrode 117 is provided for detecting the partial pressure of oxygen within the vessel 111.

As explained fully in U.S. Pat. No. 4,304,488, a light source 21 is provided in the apparatus of FIG. 1, along with condensing lenses 23, 25 and 27. These direct a concentrated beam of light upon the vessel 111 to cause part of the incident light to be absorbed selectively by the solution in the vessel 111 and a further part to be transmitted through said solution to be detected and relied upon for blood oxygen analysis. Preferably this system should be arranged to direct the light through the solution at a position adjacent end of the Clark electrode 117.

The light passing through the solution contained in the vessel 111 proceeds through a further lens 29 to a semi-silvered mirror 31 which is positioned substantially at a 45° angle and arranged to reflect substantially half the light impinging thereon and to transmit substantially half the incident light arriving through lens 29. The transmitted half of the light proceeds through a selected filter 33 to a first photoelectric cell 35, and the reflected light proceeds through filter 37 to photoelectric cell 39.

Filter 33 is arranged to respond selectively to a strong component of light present in oxygen-rich red blood, for example, a wave length of 577 millimicrons. The other filter 37 is arranged to respond to a wave length of light at which the light transmitted through the solution is of about equal intensity whether the blood is oxygen enriched or deficient in oxygen. An example of such a wave length is 586 millimicrons. The signal comparing circuit 43 in FIG. 1 responds by producing an increasing output as the output from photoelectric cell 35 increases relative to the output of the photoelectric cell 39 which is relied on for a reference level, and the thus varying signal ouput of comparing circuit 43 is supplied to the Y control input terminals of an X-Y plotter 45 having a servo-driven vertical element 47 and a servo-driven Y axis responder 49 carrying the stylus 51.

The output potential of the Clark electrode 117 varies in accordance with the partial pressure of oxygen contained within the vessel 111. The output from the Clark electrode 117 is amplified in amplifier 53 and the resulting output signal which varies as a function of the oxygen partial pressure is used to control the X control input circuit of the X-Y plotter 45.

In accordance with the explanation in U.S. Pat. No. 4,304,488, the solution 55 contained within the vessel 111 is a physiologically balanced medium such as buffered serum substitute. Preferably, the solution 55 is a 0.9% saline solution containing 5 millimolar of sodium phosphate. One buffered serum substitute solution which has been found suitable is as follows:

Sodium Chloride: 100 millimolar
Potassium Chloride: 5 millimolar
Imidazole Buffer: 30 millimolar
Sodium Phosphate: 5 millimolar
Glucose: 5 millimolar The imidazole component of this isotonic solution is a chemical compound listed in the Merck index. It provides for high stability of the pH, at 7.4 at 37° C.

Referring especially to FIG. 2, the transparent vessel 111 is formed in a block of transparent material which preferably is clear plastic material 112, as for example, an acrylic plastic or a polycarbonate. A cavity 113, which preferably is a cylindrical cavity, is formed as by providing a polished cylindrical bore, or a molded cylindrical inner surface, forming a cavity extending vertically downward within the plastic block 112 to a bottom surface 114 near the bottom of the block 112.

The Clark electrode 117 is seated in a substantially horizontal bore provided for it in the block 112, and is arranged for its sensitive electrode portion to project into the interior of the cavity 113, at 118. A horizontally directed, fine bore gas inlet 115 is provided for introducing the exchange gas immediately adjacent the bottom surface 114 of the cavity 113, and in a direction substantially radial with respect thereto. The external fitting through which gas is led to the fine-bore passage 115 is a threaded inlet port 116. A vent line 119 is provided in a top closure 120 of the cavity 113.

The diameter of the gas introduction bore 115 may be of the order of 0.5 millimeters.

The transparent block 112 admits of the introduction of light from one side along the light path axis 121, the light emerging from the opposite wall of the block 112 after passage through the blood sample in the specially prepared serum substitute solution, contained in the cavity 113.

Examples of suitable dimensions for the block 112 are:

Height: $2\frac{1}{4}''$
Width: $2\frac{1}{4}''$
Thickness: $\frac{5}{8}''$
Diameter of cavity 113: $\frac{1}{2}''$
Length of cavity 113: $1\frac{7}{8}''$
Suitable depth of the solution: $1\frac{1}{4}''$ Reference may be had to U.S. Pat. No. 4,304,488 for a more detailed description of apparatus suitable for making use of the cuvette. FIGS. 1 and 5 of said patent show the overall apparatus in which the cuvette of the present FIG. 1 herein may be used instead of the cuvette of FIG. 2 of said patent.

The cuvette of FIG. 1 hereof, as described herein, does not require any mechanical agitating means such as the mechanical agitator including motor 59, drive magnet 61 and agitator slave magnet 65 of the aforementioned U.S. Pat. No. 4,304,488. The present cuvette, with its very small volume, and its agitation by the gas introduced in the manner herein described, provides greatly accelerated operation when substituted for the cuvette of FIG. 2 of said U.S. Pat. No. 4,304,488. For example, a blood oxygen association curve may be run using the improved cuvette of the present invention in a running time of approximately five minutes, as compared to the twenty minute run provided with the cuvette shown in said patent.

Thus, the present invention offers further simplicity of construction and speed of use, and protection against any possible injury to the hemoglobin, in comparison to the cuvette shown and described in U.S. Pat. No. 4,304,488.

While in the foregoing there has been disclosed a preferred embodiment of the invention, it should be understood that various changes and modifications can be made within the true spirit and scope of the invention as recited in the appended claims.

What is claimed is:

1. An improved cuvette for use in blood oxygen association analysis comprising:
   a generally rectangular block of transparent material having a downwardly-extending cavity therein,
   an oxygen partial pressure electrode seated in said block and having its sensitive probe end extending to the interior of the cavity,
   a gas inlet formed in said block including a small-bore passage extending substantially horizontally into communication with the wall of said cavity adjacent to the bottom thereof for introduction of an exchange gas into the contents of the cavity and for agitation of its contents, and
   gas vent means at the top of said cavity for venting gas therefrom as new gas is being introduced through the gas inlet port in said block.

2. Apparatus as defined in claim 1, wherein the physical form of said cavity is a right circular cylinder, and said oxygen partial pressure electrode extends to said cavity through its cylindrical wall in a region substantially higher than the bottom thereof.

3. Apparatus as defined in claim 2, wherein the proportions of the diameter and length of said cavity are approximately $\frac{2}{3}$ inch to $1\frac{7}{8}$ inch.

4. Apparatus as defined in claim 1, wherein said block comprises a transparent plastic body.

* * * * *

UNITED STATES PATENT AND TRADEMARK OFFICE
CERTIFICATE OF CORRECTION

PATENT NO. : 4,411,523

DATED : October 25, 1983

INVENTOR(S) : Horst K. Blume, Toshio Asakura

It is certified that error appears in the above-identified patent and that said Letters Patent is hereby corrected as shown below:

Column 4, line 41 please change:

"approximately 2/3 inch" to "approximately 1/2 inch"

Signed and Sealed this

Twenty-fourth Day of January 1984

[SEAL]

Attest:

GERALD J. MOSSINGHOFF

Attesting Officer     Commissioner of Patents and Trademarks